(12) United States Patent
Nakajima

(10) Patent No.: US 7,348,166 B2
(45) Date of Patent: Mar. 25, 2008

(54) ANTI-TUMOR SUBSTANCES

(76) Inventor: Motohiro Nakajima, 1425-3 Ureshino-cho, Matsuka-shi (JP)

( * ) Notice: Subject to any disclaimer, the term of this patent is extended or adjusted under 35 U.S.C. 154(b) by 0 days.

(21) Appl. No.: 11/223,561

(22) Filed: Sep. 9, 2005

(65) Prior Publication Data

US 2006/0258743 A1    Nov. 16, 2006

(30) Foreign Application Priority Data

May 12, 2005 (JP) ............................. 2005-139678
Jul. 12, 2005 (JP) ............................. 2005-203269

(51) Int. Cl.
*C12P 7/62* (2006.01)

(52) U.S. Cl. .................. 435/135; 435/133; 435/134; 435/883

(58) Field of Classification Search ............... 554/227; 435/134, 882
See application file for complete search history.

(56) References Cited

U.S. PATENT DOCUMENTS

2006/0008850 A1*  1/2006  Riggs-Sauthier et al. .... 435/7.1

FOREIGN PATENT DOCUMENTS

| JP | 10-276790 | 10/1998 |
| JP | 2000-327579 | 11/2000 |
| JP | 2001-026549 | 1/2001 |

OTHER PUBLICATIONS

Weil et al., *Nonionic Wetting Agents*, Journal of The American Oil Chemists Society, vol. 56; pp. 873-877, 1979.

* cited by examiner

*Primary Examiner*—Deborah D. Carr
(74) *Attorney, Agent, or Firm*—Conley Rose, P.C.

(57) ABSTRACT

An anti-tumor substance may be produced from a tumor cell-derived material by *Staphylococcus*. The anti-tumor substance may include a chemical compound having the formula:

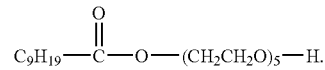

*Staphylococcus* may preferably be *Staphylococcus lentus*. Further, the tumor cell-derived material may preferably be an Ehrlich tumor cell-derived material.

2 Claims, 4 Drawing Sheets

ANTI-TUMOR SUBSTANCES

BACKGROUND OF THE INVENTION

1. Field of the Invention

The present invention relates to anti-tumor substances or compositions (tumor cell degeneration substances). More particularly, the present invention relates to anti-tumor substances produced or synthesized from tumor cell-derived materials (materials of tumor cell origin) by *Staphylococcus*. Moreover, the present invention relates to the use of anti-tumor substances in treating tumors or inhibiting tumor cell growth and methods of producing such substances.

2. Description of the Related Art

Various types of anti-tumor substances are already known. Typically, such known anti-tumor substances are chemically synthesized or simply extracted from non-tumor organisms. Also, it is known that some of the known anti-tumor substances can be bacterially produced from tumor cell-derived materials.

The use of bacteria in the production of the anti-tumor substances was first presented by the present inventor. A method for bacterially producing a special anti-tumor substance is taught, for example, by Japanese Patent Number 3088680 (Japanese Laid-Open Patent Publication Number 10-276790) that was issued to the present inventor. In this known art, Ehrlich tumor cell derived materials are decomposed by *Serratia* so that the special anti-tumor substance is produced. The anti-tumor substance thus produced has anti-tumor activity in tumor cells.

There is currently significant interest in new types of anti-tumor substances and methods of bacterially producing such anti-tumor substances. In other words, there is a need for relatively effective anti-tumor substances for inhibiting tumor cell growth. At the same time, there is a need for methods that can easily and efficiently produce such anti-tumor substances.

SUMMARY OF THE INVENTION

It is, accordingly, an object of the present teachings to provide new types of anti-tumor substances or compositions and methods for producing such substances.

In one aspect of the present teachings, an anti-tumor substance may be produced from a tumor cell-derived material by *Staphylococcus*. The anti-tumor substance may include a chemical compound having the formula:

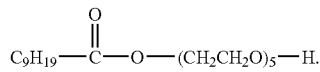

*Staphylococcus* may preferably be *Staphylococcus lentus*. Further, the tumor cell-derived material may preferably be an Ehrlich tumor cell-derived material.

The anti-tumor substance may have strong anti-tumor activity in human malignant tumors such as carcinomas and sarcomas. Further, the anti-tumor substance may have fewer side effects.

Additional objects, features and advantages of the present teachings will be readily understood after reading the following detailed description together with the accompanying drawings and the claims.

DETAILED DESCRIPTION OF THE INVENTION

Figure 1:
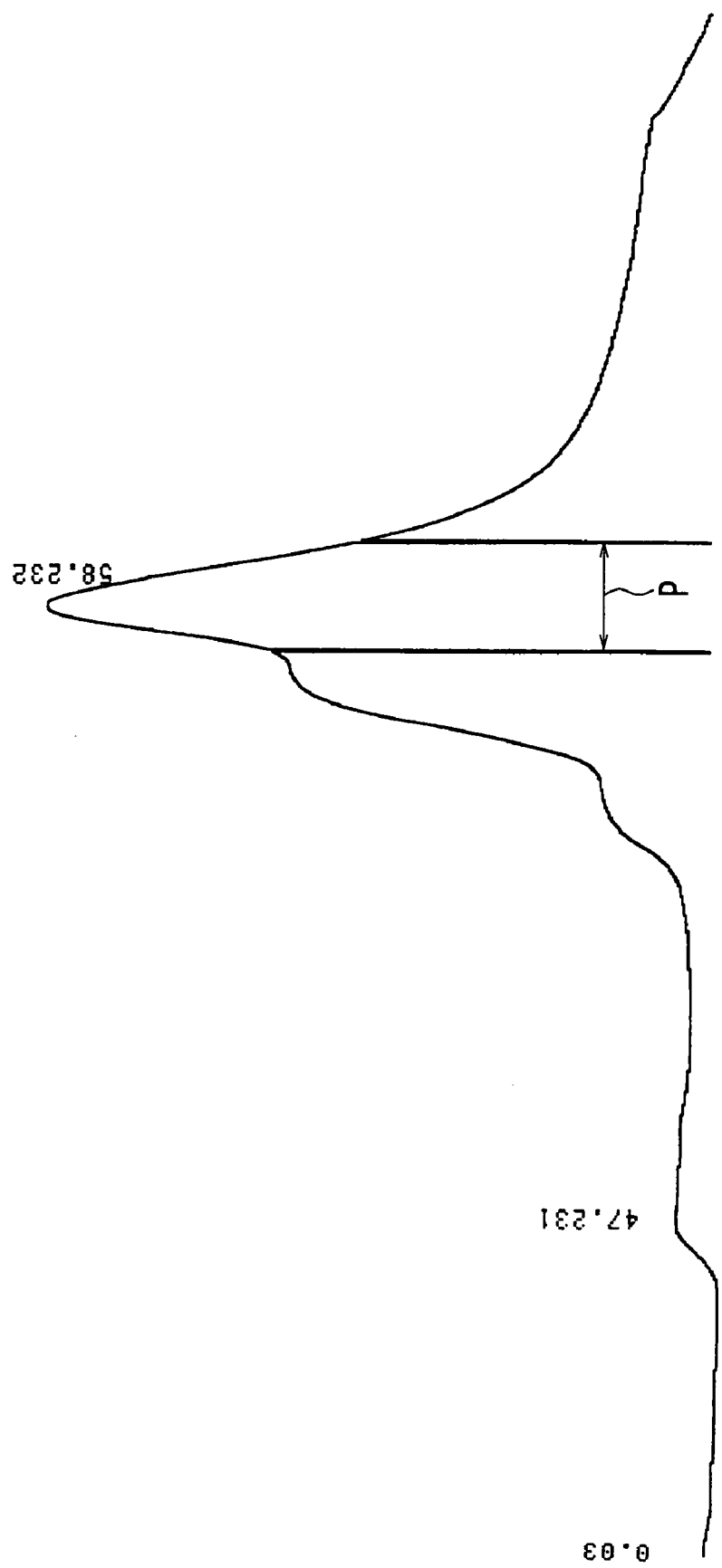
FIG. 1 is an HPLC chromatogram of Sample 1 in an embodiment according to the present invention.

A representative embodiment of the present teachings will now be described in further detail with reference to FIGS. 1 to 6. Further, in this embodiment, the term "an anti-tumor substance" refers to a substance that has anti-tumor performance against malignant tumors such as carcinomas and sarcomas.

In the past, the present inventor conducted in vivo culture examinations of Ehrlich tumor cells. In the culture examinations, Ehrlich tumor cells were transplanted into a plurality of mice contained in the same strain in order to culture the tumor cells. (Typically, fifty thousand (50,000) Ehrlich tumor cells were continuously transplanted into the mice five times.). During the examinations, the inventor noted that a group of mice did not develop any carcinomas. As a result of tests of intestinal bacterial floras of these mice, it was found that all of these mice had bacterial floras of "*Staphylococcus lentus*" only. (These mice had a survival time of approximately 2 years.) Based on this finding, it was assumed that *Staphylococcus lentus* may possibly decompose materials derived from Ehrlich tumor cells, thereby producing a useful anti-tumor substance. Thus, the inventor conceived to produce a new anti-tumor substance from the Ehrlich tumor cell-derived materials with the aid of *Staphylococcus lentus*.

The following embodiment shows that a substance or composition produced from the Ehrlich tumor cell-derived materials by *Staphylococcus lentus* may inhibit tumor cell growth without producing any adverse effects. Further, this embodiment is illustrative and not intended to be limiting of the invention.

Production Process of Anti-Tumor Substance

First, Ehrlich tumor cells (which are sometimes referred to as "mouse ascites fluid carcinoma cells") were cultured in abdominal cavities of mice of a strain of DDY (German Mouse; Tokyo University's Institute of Medical Science and National Institute of Preventive Medicine). After the sufficient culturing, ascites fluids were harvested from the abdominal cavities of the mice. The harvested ascites fluids were collected and centrifuged (10 minutes at 3000 rpm) to remove Ehrlich tumor cells therefrom, thereby producing a cell free ascites fluid that was free from Ehrlich tumor cells. As will be appreciated, the cell free ascites fluid thus produced may contain the Ehrlich tumor cell-derived materials. Thereafter, *Staphylococcus lentus* was cultured in 500 ml of the obtained cell free ascites fluid for one week at 35.5° C. so as to produce a *Staphylococcus lentus* culture fluid (a culture ascites fluid). It is expected that during this culturing operation, *Staphylococcus lentus* may possibly decompose the Ehrlich tumor cell-derived materials (i.e., tumor cell-derived materials) contained in the cell free ascites fluid, thereby producing an anti-tumor substance (i.e., an anti-tumor composition) in the cell free ascites fluid. Further, it is considered that *Staphylococcus lentus* may produce some active enzymes that can positively participate in the production of the anti-tumor substance.

In addition, it is expected that *Staphylococcus lentus* may have a large capacity to produce the anti-tumor substance because *Staphylococcus* generally has excellent bacterial reproductivity. Therefore, it is expected that *Staphylococcus lentus* may effectively decompose the Ehrlich tumor cell-derived materials such that a large amount of anti-tumor substance can be produced.

Extraction Process of Anti-Tumor Substance

The *Staphylococcus lentus* culture fluid obtained as described above was sterilized under increased temperature and pressure by utilizing an autoclave. The sterilized *Staphylococcus lentus* culture fluid was then treated with ethanol (ethyl alcohol) in order to precipitate or flocculate foreign substances or impurities therefrom, thereby formulating an ethanol-treated (alcoholized) culture fluid having approximately 80% ethanol concentration. (For example, 20 ml of the sterilized *Staphylococcus lentus* culture fluid was mixed with 80 ml of ethanol.) Subsequently, the formulated alcoholized culture fluid was filtered with a filter paper (No. 2 filter paper manufactured by Toyo Filter Paper, Japan) in order to remove precipitates of the impurities therefrom. A filtrate (a filtered fluid) of the alcoholized culture fluid Thereafter, the obtained ethanol-removed culture fluid was diluted with distilled water, thereby producing a water diluted ethanol-removed culture fluid. The water diluted ethanol-removed culture fluid was then treated with acetone in order to further precipitate or flocculate other foreign substances or impurities therefrom, thereby formulating an acetone-treated culture fluid having approximately 80% acetone concentration. (For example, 20 ml of the diluted ethanol-removed culture fluid was mixed with 80 ml of acetone.) Subsequently, the formulated acetone-treated culture fluid was filtered with a filter paper (No. 2 filter paper; Toyo Filter Paper, Japan) in order to remove precipitates of the impurities therefrom. A filtrate of the acetone-treated culture fluid was then heated in order to remove or evaporate acetone therefrom, thereby producing an acetone-removed or purified culture fluid.

Subsequently, the obtained purified culture fluid was diluted with distilled water so as to produce a water diluted purified culture fluid. Chloroform was then added to the water diluted purified culture fluid so as to produce a mixture. The mixture thus produced was shaken so as to be separated into an organic phase (chloroform phase) and a water phase. It is expected that the anti-tumor substance may preferably be transferred to the organic phase.

Separation Process of Anti-Tumor Substance

The organic phase obtained as described above was heated in order to remove or evaporate chloroform therefrom, thereby producing an organic phase condensate. It is expected that the anti-tumor substance was condensed in the condensate. The condensate thus obtained was diluted with distilled water, thereby formulating an aqueous solution of the condensate. The aqueous solution of the condensate was filtered with a filter of 0.45 micrometer. A filtrate of the condensate aqueous solution was then fractionated via a paper chromatography (PC). In the paper chromatography, a descending method was used. Further, a solution of butanol (butyl alcohol), acetic acid and water (butanol:acetic acid: purified water=4:2:1) was used as a development solution for the chromatography.

Subsequently, a specific fraction having an $R_f$ value ranging from 0.02 to 0.12 was taken as Sample 1. (The fraction can be easily collected because it has a relatively large $R_f$ value.) The collected fraction (Sample 1) was added with a desired amount of distilled water so that the anti-tumor substance was eluted or extracted thereinto. The water added fraction was then heated so as to formulate a condensed fraction fluid having the volume of 10 ml. The formulated condensed fraction fluid (10 ml) was added with 90 ml of methanol (methyl alcohol) and was sufficiently stirred so as to have an approximately 90% methanol concentration. Subsequently, the alcoholized fraction fluid thus obtained was stored in a cold room at 1-5° C. for 24 hours. The alcoholized stored fraction fluid was centrifuged (10 minutes at 3000 rpm) and was then heated in order to remove or evaporate methanol therefrom, thereby producing a final anti-tumor substance containing fluid. The final anti-tumor substance containing fluid thus obtained was taken as Sample 2.

Purification and Analysis Process of Anti-Tumor Substance

Sample 1 (i.e., the fraction having an $R_f$ value ranging from 0.02 to 0.12) obtained in the above-described separation process was purified and analyzed by a High Performance Liquid Chromatography (HPLC). Purification and analysis of the fraction by the HPLC was performed under following conditions.

HPLC Operating Condition

Instrument Type: Shimazu LC-10A

Column: COSMOSIL vC18

Column Size: 20 mm (I.D.)×250 mm (Length)

Mobile Phase: 30% Methanol Aqueous Solution

Detection Wavelength: 210 nm (λ=210)

Flow Rate: 0.8 ml/min

Column Temperature: 30° C.

A chromatogram obtained as a result of the HPLC of Sample 1 is shown in FIG. 1. As is evident from the chromatogram, it is considered that a region P of the chromatogram corresponds to the anti-tumor substance. Therefore, it is presumed that Sample 1 can be further treated by a commonly used purification method (e.g., an extraction method) so as to further purify the anti-tumor substance.

Determination of Molecular Weight and Molecular Structure of Chemical Compounds Constituting Anti-Tumor Substance Sample 1 (i.e., the fraction having an $R_f$ value ranging from 0.02 to 0.12) obtained in the above-described separation process was analyzed by a Liquid Chromatograph Mass Spectrometer (LC/MS) in order to determine a molecular weight and a molecular structure of chemical compounds that constitute the anti-tumor substance. Determination of the molecular weight and the molecular structure of the chemical compounds was performed under the following conditions.

Figure 2:
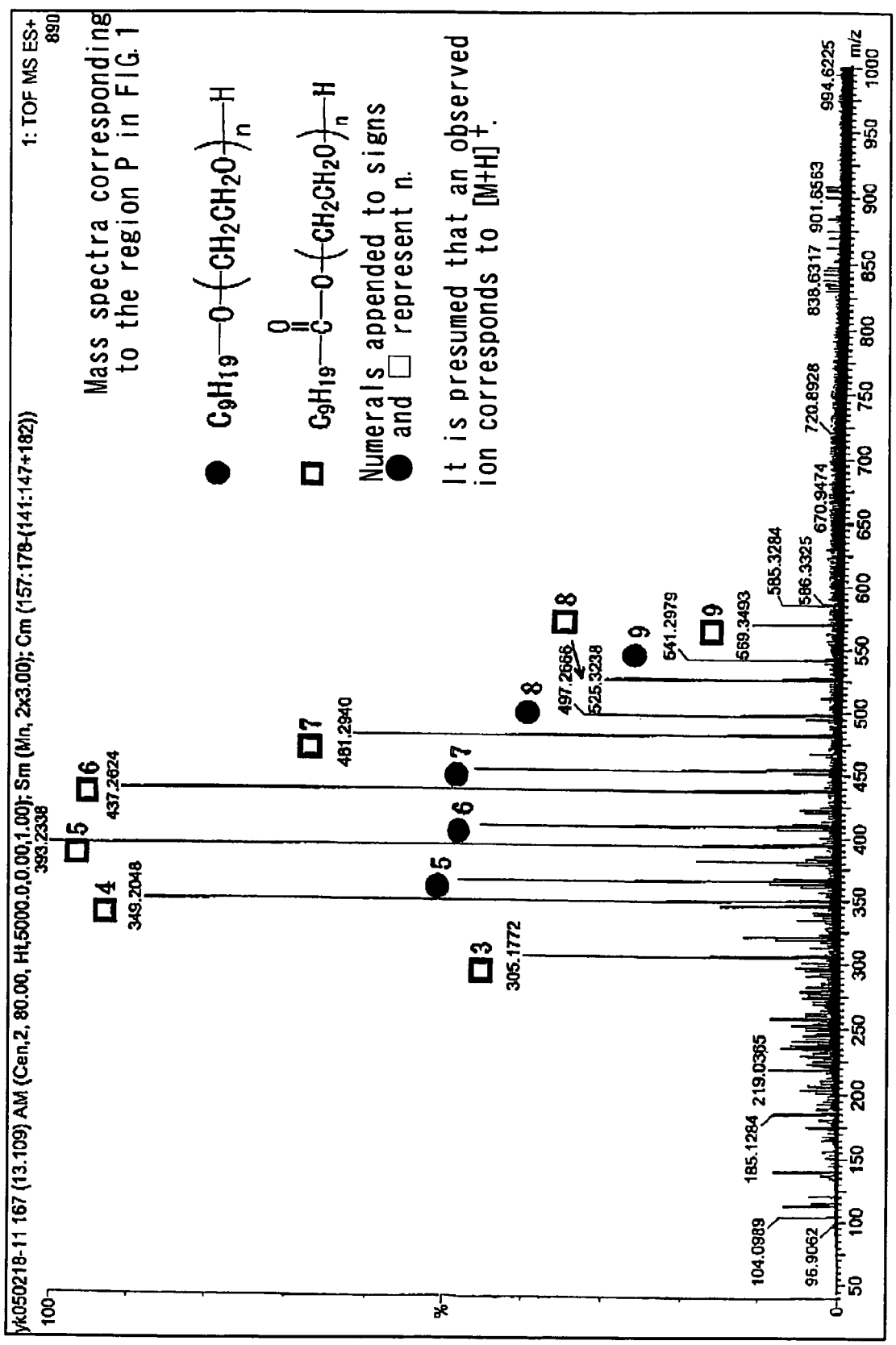
FIG. 2 is an LC/MS mass spectra of Sample 1.

LC/MS Operating Conditions
(1) LC (HPLC)
Instrument Type: Waters 2690
Column: Asahipak GS-101H
Column Size: 4.6 mm (I.D.)×250 mm (Length)
Mobile Phase: 30% Methanol Aqueous Solution
Flow Rate: 1 ml/mm
Column Temperature: 30° C.
* The mobile phase passed through the column was introduced into the MS in fractional amounts.
(2) MS
Instrument Type: Micromass Q-Tof
Column Temperature: 30° C.
Sample Concentration: 3 mg/ml
Injection Rate: 10 microliter
Ionization Method: ESI Positive
Mass Measurement Range: 40-1000 AMU (Atomic Mass Unit)
Capillary Voltage: 3000 V
Cone Voltage: 30 V
Source Block Temperature: 80° C.
Desolvation Temperature: 350° C.
Read Time: 2 seconds Mass spectra obtained as a result of the LC/MS of Sample 1 is shown in FIG. 2. As will be appreciated, the mass spectra corresponds to the region P of the chromatogram in FIG. 1. From the mass spectra, it is confirmed that the anti-tumor substance basically consists of a plurality of chemical compounds having the following general formula:

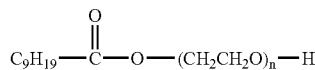

wherein n is an integer from 3 to 9.

Further, as will be apparent from the mass spectra, a main component of the anti-tumor substance is a chemical compound having the following formula:

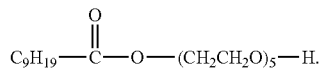

The main chemical compound as defined by the above-described formula is named "decanoic acid 14-hydroxy-3,6,9,12-tetraoxatetradec-1-yl ester (9CI)" or "pentaethylene glycol monodecanoate." In addition, the molecular weight of this main chemical compound is 392.52.

In Vivo Evaluation of Anti-Tumor Substance

The anti-tumor substance containing fluid produced as Sample 2 in the separation process described above was diluted with distilled water, thereby producing an aqueous solution of the anti-tumor substance (i.e., an experimental anti-tumor solution). The anti-tumor substance concentration of the formulated experimental anti-tumor solution was 10 mg/10 ml.

Twenty (20) mice of the strain of DDY were respectively inoculated with about $10^6$ of Ehrlich tumor cells (the mouse ascites fluid carcinoma cells). That is, about $10^6$ of Ehrlich tumor cells was injected into an abdominal cavity of each mouse. After twenty four (24) hours, these mice were divided two groups, i.e., a testing group of ten (10) mice and a control group of ten (10) mice. Thereafter, the mice of the testing group were respectively treated with about 0.5 ml of the experimental anti-tumor solution. That is, about 0.5 ml of the experimental anti-tumor solution was administered into the abdominal cavity of each mouse of the testing group. Conversely, the mice of the control group were respectively treated with about 0.5 ml of saline. That is, about 0.5 ml of saline was administered into the abdominal cavity of each mouse of the control group.

In two (2), five (5) and fifteen (15) hours after the administration of the experimental anti-tumor solution and saline, ascites fluids were harvested from the abdominal cavities of the mice of respective groups. Thereafter, Ehrlich tumor cells contained in the harvested ascites fluids were stained by utilizing a Giemsa staining method so as to microscopically observe a degeneration process of Ehrlich tumor cells.

Results of Testing

Figure 3:
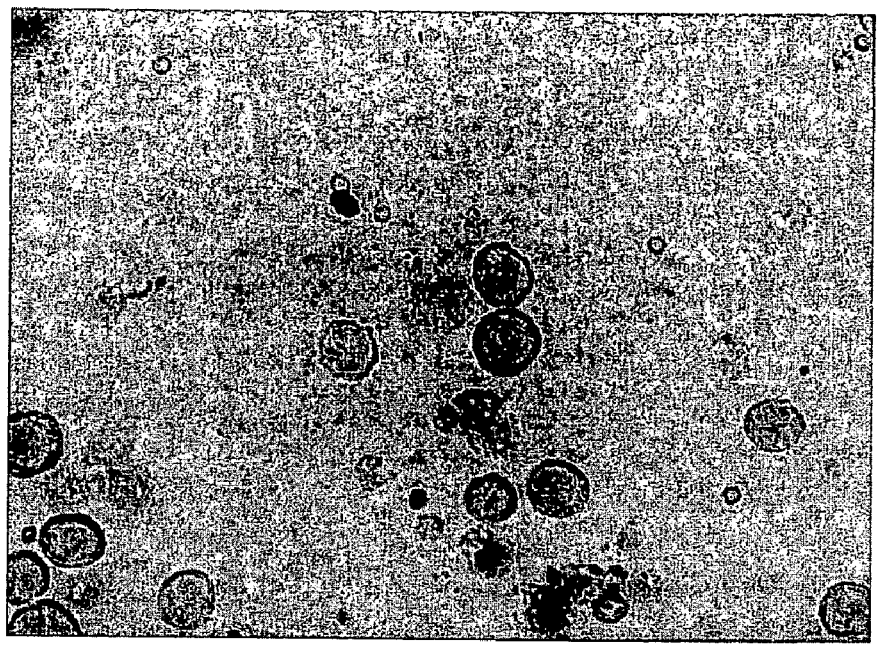
FIG. 3 is a micrograph of Ehrlich tumor cells in ascites fluids of a control mouse, which illustrates a condition immediately after saline was administered into an abdominal cavity of the control mouse.

As shown in FIG. 3, in immediately after the administration of saline, Ehrlich tumor cells contained in the ascites fluid of one of the mice of the control group were not at all degenerated. That is, there was no trace of degeneration of Ehrlich tumor cells. In addition, although not shown in the drawings, in two, five and fifteen hours after the administration of saline, Ehrlich tumor cells contained in the ascites fluids of the control mice were not degenerated. Thus, in the mice of the control group, the degeneration of Ehrlich tumor cells was not observed.

Figure 4:
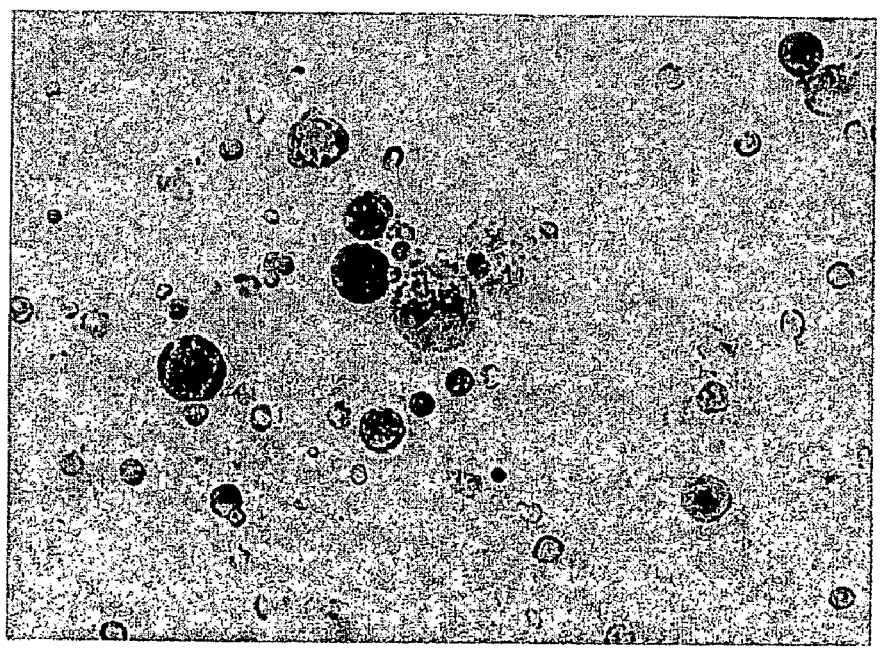
FIG. 4 is a micrograph of Ehrlich tumor cells in ascites fluids of a testing mouse, which illustrates a condition in two hours after an experimental anti-tumor solution was administered into an abdominal cavity of the testing mouse.
Figure 5:
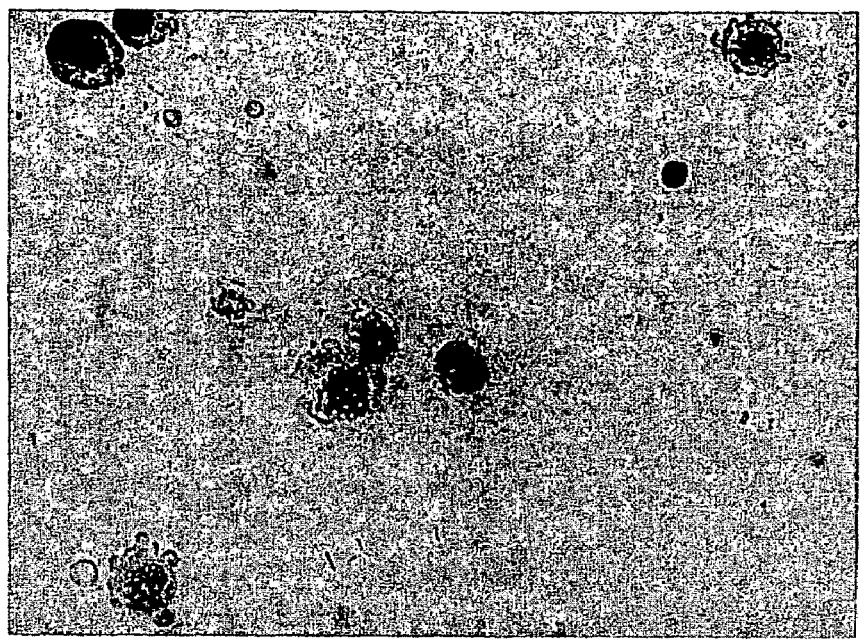
FIG. 5 is a micrograph of Ehrlich tumor cells in the ascites fluids of the testing mouse, which illustrates a condition in five hours after the experimental anti-tumor solution was administered into the abdominal cavity of the testing mouse.
Figure 6:
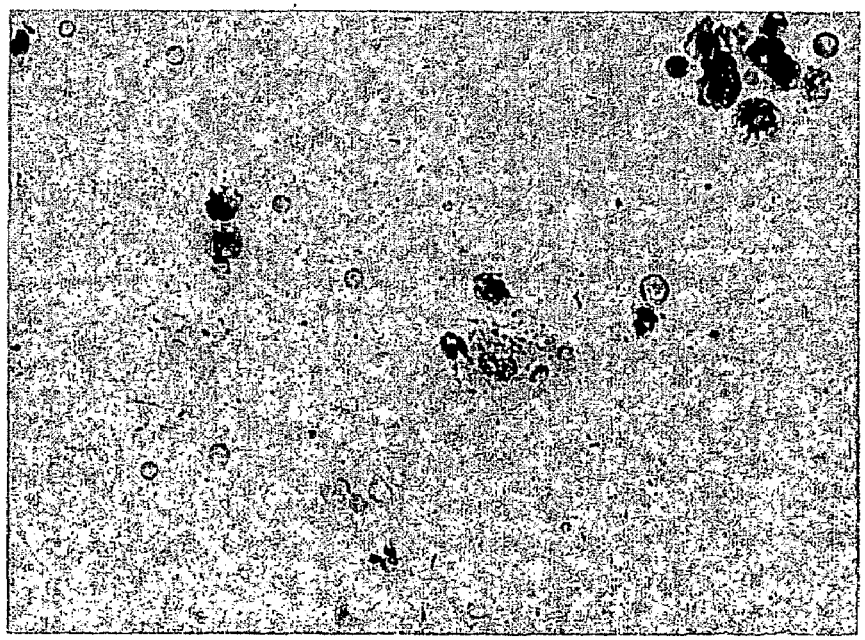
FIG. 6 is a micrograph of Ehrlich tumor cells in the ascites fluids of the testing mouse, which illustrates a condition in fifteen hours after the experimental anti-tumor solution was administered into the abdominal cavity of the testing mouse.

Conversely, as shown in FIG. 4, it was observed that in two hours after the administration of the experimental anti-tumor solution, some of Ehrlich tumor cells (stained cells) of the mice of the testing group were partly degraded or destroyed. As shown in FIG. 5, it was observed that in five hours after the administration of the experimental anti-tumor solution, increased numbers of Ehrlich tumor cells of the testing mice were destroyed. Further, as shown in FIG. 6, it was observed that in fifteen hours after the administration of the experimental anti-tumor solution, all of Ehrlich tumor cells of the testing mice were destroyed. Thus, in the mice of the testing group, it was observed that Ehrlich tumor cells were degraded over time. These data suggest that the anti-tumor substance (the anti-tumor composition) contained in the experimental anti-tumor solution may affect Ehrlich tumor cells so as to induce breakdown or disruption of cell nucleus thereof. These results clearly indicate that the anti-tumor substance of the present embodiment is effective to mouse carcinoma cells. Therefore, it is considered that the present anti-tumor substance may probably have strong anti-tumor activity in human malignant tumors such as carcinomas and sarcomas.

A further study was conducted in order to determine the expected side effects of the anti-tumor substance. However, none of the mice of the testing group demonstrated symptoms of side effects. Therefore, it is expected that the present anti-tumor substance may be a useful or effective anti-tumor substance free of side effects.

An additional study was conducted in order to demonstrate any survival advantage of the anti-tumor substance. It was observed that the mice of the control group have a survival time of 7-12 days whereas the mice of the testing group have a survival time of 21 days. These results clearly indicate that the present anti-tumor substance shows a good survival benefit for the tested mice.

According to the present embodiment, the anti-tumor substance may be biosynthesized by utilizing organisms (bacterial enzymes). Therefore, the anti-tumor substance can be efficiently produced.

Further, the anti-tumor substance obtained in this embodiment has a good heat resistance, pressure resistance, oxidation resistance at room temperature or other such properties. That is, the obtained anti-tumor substance has a relatively better adaptability for environmental conditions than the prior art anti-tumor substances. Therefore, the anti-tumor substance obtained in this embodiment is easy to use.

Further, although the Ehrlich tumor cell-derived materials are used as the tumor cell-derived materials in this embodiment, other materials that are derived from HeLa tumor cells, HEP-2 tumor cells, Sarcoma-180 tumor cells or other such tumor cells can be used.

Also, in this embodiment, it is demonstrated that the present anti-tumor substance is effective to Ehrlich tumor cells (i.e., the ascites fluid carcinoma cells). Therefore, it is considered that such an anti-tumor substance has an excellent potential to be effective to solid carcinomas, various adenocarcinomas, squamous carcinomas, anaplastic carcinomas or other such carcinomas and sarcomas.

Moreover, in this embodiment, the anti-tumor substance is directly administered to the target carcinoma cells. However, the present anti-tumor substance can be administered by oral administration, nasal administration, mucosal administration, enteral administration, intravenous administration (drip administration), hypodermic administration or other such administration. That is, the anti-tumor substance can be formulated as preparations in the form of tablets, granules, slow-release capsules, suppositories, nasal spray liquids, injection solutions or drip liquids.

A representative example of the present teachings has been described in detail with reference to the attached drawings. This detailed description is merely intended to teach a person of skill in the art further details for practicing preferred aspects of the present teachings and is not intended to limit the scope of the invention. Only the claims define the scope of the claimed invention. Therefore, combinations of features and steps disclosed in the foregoing detailed description may not be necessary to practice the invention in the broadest sense, and are instead taught merely to particularly describe detailed representative examples of the invention. Moreover, the various features taught in this specification may be combined in ways that are not specifically enumerated in order to obtain additional useful embodiments of the present teachings.

What is claimed is:

1. A method of producing an anti-tumor substance, the method comprising:

culturing tumor cells in an ascites fluid, thereby producing an Ehrlich tumor cell-derived material in the ascites fluid; and culturing *Staphylococcus lentus* in the ascites fluid that contains the Ehrlich tumor cell-derived material, thereby producing the anti-tumor substance in the ascites fluid, wherein the anti-tumor substance comprises a compound having the formula,

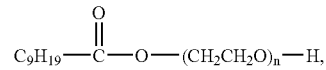

$$C_9H_{19}-\overset{O}{\underset{\|}{C}}-O-(CH_2CH_2O)_n-H,$$

wherein n is an integer from 3 to 9.

2. The method as defined in claim 1 further comprising extracting the anti-tumor substance from the ascites fluid and separating the anti-tumor substance.

* * * * *